US010279071B2

(12) United States Patent
Sa et al.

(10) Patent No.: US 10,279,071 B2
(45) Date of Patent: May 7, 2019

(54) ALDEHYDE CONTROL IN PERSONAL CARE PRODUCTS

(71) Applicant: Kimberly-Clark Worldwide, Inc., Neenah, WI (US)

(72) Inventors: InYoung Sa, GyeongGi-Do (KR); SiOn Choi, GyeongGi-Do (KR); Matthew John Valaskey, Neenah, WI (US); HyoungKun Park, GyeongGi-Do (KR); JungHyun Choi, GyeongGi-Do (KR); John Gavin MacDonald, Decatur, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 554 days.

(21) Appl. No.: 15/187,024

(22) Filed: Jun. 20, 2016

(65) Prior Publication Data
US 2016/0303274 A1    Oct. 20, 2016

Related U.S. Application Data

(63) Continuation of application No. 13/781,238, filed on Feb. 28, 2013, now Pat. No. 9,393,164.

(51) Int. Cl.
*A61F 13/84*    (2006.01)
*A61L 15/46*    (2006.01)
(Continued)

(52) U.S. Cl.
CPC .......... *A61L 15/46* (2013.01); *A61F 13/8405* (2013.01); *A61L 15/18* (2013.01);
(Continued)

(58) Field of Classification Search
CPC ............ A61F 13/51113; A61F 13/8405; A61F 2013/51059; A61F 2013/51066;
(Continued)

(56) References Cited

U.S. PATENT DOCUMENTS 821,722 A    5/1906    Lindsay
4,529,623 A    7/1985    Maggs
(Continued)

FOREIGN PATENT DOCUMENTS

CN    202311289 U    7/2012
EP    0311364 B1    10/1992
(Continued)

OTHER PUBLICATIONS

Hightower, Mike and Gary Brown, "Evaporation Suppression Research and Applications for Water Management," Identifying Technologies to Improve Regional Water Stewardship: North-Middle Rio Grande Corridor, Apr. 21-22, 2004, pp. 76-83.
(Continued)

*Primary Examiner* — Catharine L Anderson
(74) *Attorney, Agent, or Firm* — Kimberly-Clark Worldwide, Inc.

(57) ABSTRACT

An odor control layer for personal care products has a composition that has a PEG or PEG copolymer composition applied thereto. The layer can be placed in a personal care product, such as a diaper, training pant, absorbent under pant, adult incontinence product, or feminine hygiene product. Additional odor control layers may include silver nanoparticles and activated carbon compositions. In an alternative form, a single odor control layer includes the PEG composition and the activated carbon and/or silver nanoparticle compositions. A cleansing composition with PEG and possibly active carbon and silver nanoparticles may be combined with the personal care product to form a kit.

20 Claims, 10 Drawing Sheets

(51) Int. Cl.
*A61L 15/18* (2006.01)
*A61L 15/26* (2006.01)
*A61L 15/20* (2006.01)
*A61F 13/15* (2006.01)
*A61F 13/551* (2006.01)

(52) U.S. Cl.
CPC .............. *A61L 15/20* (2013.01); *A61L 15/26* (2013.01); *A61F 13/5519* (2013.01); *A61F 2013/15146* (2013.01); *A61F 2013/8408* (2013.01); *A61L 2300/104* (2013.01); *A61L 2300/108* (2013.01); *A61L 2300/20* (2013.01); *A61L 2400/12* (2013.01)

(58) Field of Classification Search
CPC .. A61F 2013/51069; A61F 2013/51073; A61F 2013/5109; A61F 2013/8408; A61F 2013/8432; A61F 2013/8455; A61L 15/46; A61L 15/48; A61L 15/50
See application file for complete search history.

(56) References Cited

U.S. PATENT DOCUMENTS

| | | | |
|---|---|---|---|
| 4,826,497 A | 5/1989 | Marcus et al. | |
| 5,498,478 A | 3/1996 | Hansen et al. | |
| 5,944,704 A | 8/1999 | Guarracino et al. | |
| 6,031,147 A | 2/2000 | Gross | |
| 6,245,693 B1 | 6/2001 | Gagliardi et al. | |
| 6,417,424 B1 | 7/2002 | Bewick-Sonntag et al. | |
| 6,559,353 B1 * | 5/2003 | Sheridan ........... A61F 13/51113 604/367 |
| 7,473,817 B1 | 1/2009 | Tanaka et al. | |
| 7,837,663 B2 | 11/2010 | MacDonald et al. | |
| 8,022,026 B2 | 9/2011 | Nguyen et al. | |
| 8,298,520 B2 | 10/2012 | Itoi et al. | |
| 2002/0035046 A1 | 3/2002 | Lukenbach et al. | |
| 2002/0188264 A1 | 12/2002 | Knuth et al. | |
| 2003/0130636 A1 * | 7/2003 | Brock ..................... A61F 13/84 604/367 |
| 2003/0155089 A1 | 8/2003 | Anderson et al. | |
| 2003/0203830 A1 | 10/2003 | Zhu et al. | |
| 2003/0206979 A1 * | 11/2003 | Dvoracek ........... A61F 13/8405 424/766 |
| 2004/0133141 A1 | 7/2004 | Kiel et al. | |
| 2005/0035327 A1 | 2/2005 | Canada et al. | |
| 2005/0113771 A1 | 5/2005 | MacDonald et al. | |
| 2006/0046943 A1 | 3/2006 | Erazo-Majewicz et al. | |
| 2006/0137568 A1 | 6/2006 | MacDonald et al. | |
| 2007/0020452 A1 | 1/2007 | Hamed et al. | |
| 2007/0060691 A1 | 3/2007 | Kim | |
| 2007/0065397 A1 | 3/2007 | Ito et al. | |
| 2007/0077428 A1 | 4/2007 | Hamed et al. | |
| 2007/0122461 A1 | 5/2007 | Ko | |
| 2007/0142264 A1 | 6/2007 | Nguyen et al. | |
| 2007/0166399 A1 | 7/2007 | Burton et al. | |
| 2008/0009812 A1 | 1/2008 | Riesinger | |
| 2008/0286224 A1 | 11/2008 | Vega et al. | |
| 2009/0062764 A1 | 3/2009 | MacDonald et al. | |
| 2009/0075060 A1 | 3/2009 | Miller et al. | |
| 2009/0105676 A1 | 4/2009 | Brusk et al. | |
| 2009/0123504 A1 | 5/2009 | Feldkamp et al. | |
| 2009/0247973 A1 | 10/2009 | Yeh et al. | |
| 2009/0275906 A1 | 11/2009 | Berland et al. | |
| 2010/0062031 A1 | 3/2010 | Yoshimasa et al. | |
| 2010/0069861 A1 | 3/2010 | Yao et al. | |
| 2010/0307422 A1 | 12/2010 | Huck et al. | |
| 2010/0324512 A1 | 12/2010 | Caputi et al. | |
| 2011/0118687 A1 | 5/2011 | Elder et al. | |
| 2011/0150959 A1 | 6/2011 | Andreasson et al. | |
| 2011/0313373 A1 | 12/2011 | Riesinger | |
| 2012/0150078 A1 | 6/2012 | Chen et al. | |
| 2012/0308507 A1 | 12/2012 | Karim et al. | |
| 2013/0164334 A1 | 6/2013 | Quincy, III et al. | |
| 2013/0237933 A1 | 9/2013 | Ko | |

FOREIGN PATENT DOCUMENTS

| | | |
|---|---|---|
| EP | 0510619 A1 | 10/1992 |
| EP | 0570430 A1 | 11/1993 |
| EP | 0933088 A1 | 8/1999 |
| EP | 1255806 A1 | 11/2002 |
| EP | 1358894 A1 | 11/2003 |
| EP | 1992366 A1 | 11/2008 |
| EP | 2163611 A1 | 3/2010 |
| EP | 1380283 B1 | 3/2011 |
| EP | 2563306 A1 | 3/2013 |
| JP | 05-161671 A | 6/1993 |
| JP | 2002-301144 A | 10/2002 |
| JP | 2003-119663 A | 4/2003 |
| JP | 2003-129088 A | 5/2003 |
| JP | 3143362 U | 7/2008 |
| JP | 2012-001551 A | 1/2012 |
| KR | 20-2009-0001530 U | 2/2009 |
| RU | 2258536 C2 | 8/2005 |
| WO | WO 1995/024173 A2 | 9/1995 |
| WO | WO 1997/046191 A1 | 12/1997 |
| WO | WO 1998/026808 A2 | 6/1998 |
| WO | WO 1998/056341 A1 | 12/1998 |
| WO | WO 2000/050099 A1 | 8/2000 |
| WO | WO 2000/051651 A1 | 9/2000 |
| WO | WO 2000/051655 A1 | 9/2000 |
| WO | WO 2003/053487 A1 | 7/2003 |
| WO | WO 2008/062291 A2 | 5/2008 |
| WO | WO 2009/006377 A1 | 1/2009 |
| WO | WO 2009/010929 A2 | 1/2009 |

OTHER PUBLICATIONS

Moosavi-Movahedi, A.A., "Thermodynamics of Protein Denaturation by Sodium Dodecyl Sulfate," Journal of the Iranian Chemical Society, vol. 2, No. 3, Sep. 2005, pp. 189-196.

* cited by examiner

ALDEHYDE CONTROL IN PERSONAL CARE PRODUCTS

CROSS-REFERENCE TO RELATED APPLICATIONS

This application is a continuation of and claims priority to U.S. patent application Ser. No. 13/781,238 filed on Feb. 28, 2013, the contents of which are incorporated herein by reference for all purposes.

BACKGROUND

The present disclosure concerns the alleviation and control of odors in personal care products, in particular, odors associated with aldehydes.

Disposable personal care products perform a needed function in today's busy society, freeing caregivers and users from the chore of washing reusable products and allowing for the quick and easy disposal of body wastes. As leakage issues have been reduced because of improved designs, the control of odors has become more important to the consumer. This is a particular concern to users of incontinence products.

Odor is often used by consumers as a signal that a personal care product should be changed. The detection of the odor depends, however, on the acuity of the sense of smell of the consumer, an acuity that often declines with age. Relying on the odor of the product also means that the odor must become offensive before the product is changed, an unacceptable signal.

Many technologies have been evaluated in an attempt to reduce the odors that emanate from these products during use. For example, an activated carbon ink printed liner for incontinence pads was recently introduced. Many urine odor ranking panel (ORP) studies have shown improvements in odor for the carbon-treated liner. However, complete elimination of odor has not been achieved with activated carbon except at levels that are not commercially viable for reasons of cost and/or migration. It is important that anything added to a personal care product to reduce odor should remain in place and not migrate through the product.

There remains a need for a treatment for absorbent articles with improved odor control.

SUMMARY

In one aspect of the disclosure is a composition for the reduction of aldehydes that includes a PEG or PEG copolymer, wherein the PEG or PEG copolymer has an n<=20.

In another aspect is a personal care product having a first aldehyde odor control layer with a PEG or a PEG copolymer composition applied thereto, wherein the PEG or PEG copolymer has an n<=20. The personal care product includes a liner and an absorbent core. The first aldehyde odor control layer is located between the liner and the absorbent core.

In yet another aspect is a kit. The kit includes a personal care product having a liquid-permeable bodyside liner; a liquid-impermeable outer cover affixed to the bodyside liner; an absorbent core disposed between the bodyside liner and the outer cover; and an aldehyde odor control layer including PEG or a PEG copolymer having an n<=20. The personal care product is a diaper, training pant, absorbent underpants, adult incontinence product, or feminine hygiene product. Included in the kit is a cleaning composition including PEG or a PEG copolymer having an n<=20 and water. The cleaning composition is contained in a waterproof package.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings, where:

Figure 1:
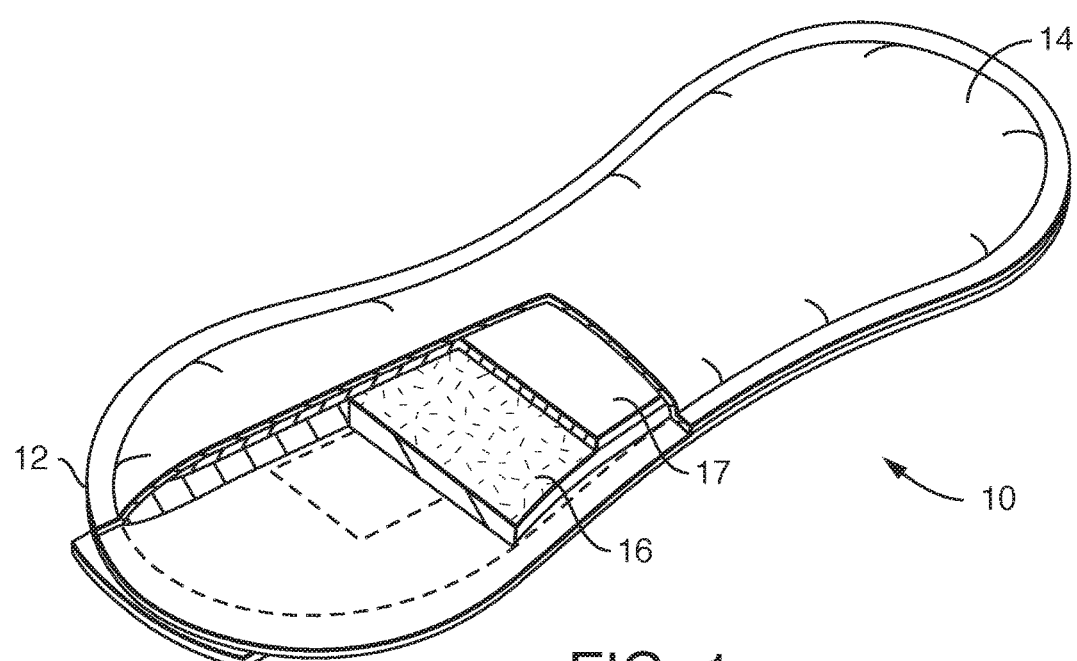
FIG. 1 is a drawing of a feminine hygiene product.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

Definitions

"Nonwoven" and "nonwoven web" refer to materials and webs of material that are formed without the aid of a textile weaving or knitting process. For example, nonwoven materials, fabrics or webs have been formed from many processes such as, for example, meltblowing processes, spunbonding processes, air laying processes, coform processes, and bonded carded web processes.

"Coform" refers to a blend of meltblown fibers and absorbent fibers such as cellulosic fibers that can be formed by air forming a meltblown polymer material while simultaneously blowing air-suspended fibers into the stream of meltblown fibers. The meltblown fibers and absorbent fibers are collected on a forming surface, such as provided by a belt. Two U.S. patents describing coform materials are U.S. Pat. No. 5,100,324 to Anderson et al. and U.S. Pat. No. 5,350,624 to Georger et al., both of which are incorporated in their entirety in a manner consistent herewith.

"Meltblown" refers to fibers formed by extruding a molten thermoplastic material through a plurality of fine, usually circular, die capillaries as molten threads or filaments into converging high velocity gas (e.g., air) streams, generally heated, which attenuate the filaments of molten thermoplastic material to reduce their diameters. Thereafter, the meltblown fibers are carried by the high velocity gas stream and are deposited on a collecting surface or support to form a web of randomly dispersed meltblown fibers. Such a process is disclosed, for example, in U.S. Pat. No. 3,849,241 to Butin et al. which is incorporated in their entirety in a manner consistent herewith.

"Spunbonded fibers" refers to small diameter fibers which are formed by extruding molten thermoplastic material as filaments from a plurality of fine, usually circular capillaries of a spinneret with the diameter of the extruded filaments then being rapidly reduced to fibers as by, for example, in U.S. Pat. No. 4,340,563 to Appel et al.; U.S. Pat. No. 3,692,618 to Dorschner et al.; U.S. Pat. No. 3,802,817 to Matsuki et al.; U.S. Pat. Nos. 3,338,992 and 3,341,394 to Kinney; U.S. Pat. No. 3,502,763 to Hartman; and U.S. Pat. No. 3,542,615 to Dobo et al., the contents of which are incorporated herein by reference in their entirety in a manner consistent herewith.

It is to be understood by one of ordinary skill in the art that the present discussion is a description of exemplary aspects of the present disclosure only, and is not intended as limiting the broader aspects of the present disclosure.

Aldehydes are the major malodor note associated with urine odor, after fresh void and a period thereafter. Thus, the control of aldehydes in personal care products is of particular interest to adults like those who wear incontinence products and the like, and to the care-givers who look after them. The desire to avoid embarrassment due to unpleasant urine odors is important to adult consumers of these products and the products described in the present disclosure help greatly in this regard.

One embodiment of the present disclosure is directed to a urine odor control composition that contains polyethylene glycol ("PEG") and/or polyethylene glycol copolymers (collectively referred to as "PEG components"). Desirably, the PEG components have a number of polymer units less than or equal to 20, $n \leq 20$. The composition is applied to select components of personal care absorbent articles.

Another embodiment of the present disclosure is directed to a urine odor control composition that contains activated carbon. It is intended that activated carbon be used in conjunction with PEG components as described herein.

Yet another embodiment of the present disclosure is directed to a urine odor control composition that contains silver nanoparticles. It is intended that silver nanoparticles be used in conjunction with the activated carbon and PEG components as described herein.

Compositions for Elimination of Aldehyde Odors

PEG Composition

In one aspect of the disclosure, a "PEG composition" includes the following ingredients: water, a PEG surfactant, a thickener, a preservative, and an optional fragrance.

The composition is about 60 to about 90%, or about 70% to about 90%, or about 80 to about 90% water. The water primarily serves as a carrier for the active ingredient, the PEG surfactant or other ingredients such as activated carbon and silver nanoparticles. Desirably, the water is distilled, though tap water may suffice.

The composition contains about 10 to about 40% PEG surfactant. Suitable PEG surfactants include a PEG or PEG copolymer that has a number of polymer units of less than or equal to 20 ($n \leq 20$), or less than or equal to 10 ($n \leq 10$), or less than or equal to 5 ($n \leq 5$). Suitable PEG or PEG copolymers having an $n \leq 20$ include: laureth-4, polysorbate 20, myreth-3 myristate, octoxynol-9, PEG-7 glyceryl cocoate, or combinations thereof.

The composition may contain about 0.5 to 10% thickener. The purpose of the thickener is to make it easier to apply to a substrate using printing methods. Should the substrate be dipped or sprayed with the composition, the thickener may not be necessary. Suitable thickeners include: Xanthan gum, Carbomer, Acrylates Crosspolymer, and PEG-150 Pentaerythrityl tetrastearate.

The composition may contain about 0.2 to 1.5% of a preservative. The purpose of the preservative is to keep the composition from spoiling before it is applied to a substrate. Suitable preservatives include: Methyl Paraben, Phenoxy Ethanol, Sodium Benzoate, Methylisothiazolinone, and 1,2 Hexanediol, Caprylyl Glycol.

Activated Carbon (AC) Composition

The AC composition is an ink formulation that basically includes activated carbon and a binder.

The unique nature of the activated carbon preferably used herein results from the small size of the particles. In one example, black ink is prepared including activated carbon particles up to 10 microns in diameter, preferably up to 5 microns in diameter, more preferably up to 2 microns in diameter, and even more preferably up to 1 micron in diameter. Ink including activated carbon particles can also be colored ink, such as those described in U.S. Pat. No. 7,531,471 to Quincy, Ill., which is incorporated herein by reference to the extent it does not conflict herewith.

For the inks used in the examples below, the black ink included activated carbon particles of approximately 1 micron in diameter, whereas the blue ink included activated carbon particles of approximately 5-10 microns to as much as 20 microns in diameter. The smaller particle size resulted in an improved odor reduction likely resulting from the increased available surface area of the smaller activated carbon particles in the black ink. It is thought that the binder in the ink forms micro-cracks as it dries, allowing access of the odor to the majority of the activated carbon particles. While a common binder would typically block adsorption of odor by a majority of the activated carbon particles, the ink binder used herein results in an activity loss of less than ten percent as compared to the activated carbon particles themselves.

Improved odor adsorption with the black ink can also result from the amount of activated carbon particles in the ink. For example, the blue ink's inclusion of larger activated carbon particles up to 20 microns in diameter or larger resulted in fewer activated carbon particles due to the need to prevent settling of the particles, which is more of a challenge with larger particles.

The use of activated carbon ink in absorbent articles is described in further detail in U.S. Pat. No. 7,816,285 to MacDonald et al. and in U.S. Pat. No. 7,655,829 to MacDonald et al., each of which is incorporated herein by reference to the extent it does not conflict herewith.

The composition of the present disclosure may include about 1% to about 5%, or about 1% to about 2.5%, or about 2.5% activated carbon.

Silver (SILV) Composition

The silver nanoparticle composition is basically made with silver nanoparticles mixed with either water (desirably distilled) or solvent.

The silver nanoparticles are preferably SILVAGARD silver nanoparticles available from AcryMed, Inc. of Beaverton, Oreg. According to AcryMed, Inc., SILVAGARD silver nanoparticles are formed chemically in a solution. The nanoparticles are uniform in size (about 10 nm) and because of proprietary technology they do not agglomerate to form large particles, but stay in suspension pending application to other materials. After the SILVAGARD silver nanoparticle solution is prepared, the substrate is contacted with the solution by immersing, spraying, printing, or by any other suitable application means. The amount of nanoparticle silver actually deposited is controlled by adjusting the silver concentration and the temperature of the solution as well as the dwell time in contact with the solution.

Because of their size, the nanoparticles attach to the surface being treated while the substrate is in contact with the SILVAGARD silver nanoparticle solution. The attachment is very uniform over the surface of the substrate. Once treated, the substrate is removed and dried. The SILVAGARD silver nanoparticles adhere tenaciously even on elastic substrates when they are stretched or flexed.

The solution treatment process can be either aqueous or solvent based, depending on the needs or characteristics of the substrate to be treated. Each nanoparticle would theoretically contain a small number (approximately 5,000) of silver atoms. The outer layer of silver in each particle oxidizes upon exposure to air or bodily fluid. This process forms a monolayer of $Ag2O$ (silver oxide) on the outside of the nanoparticle. The silver oxide then slowly dissolves in the body fluid it encounters after the substrate is applied. It dissolves to produce $Ag+$, ionic silver.

It should be noted that the SILVAGARD silver nanoparticles are applied to the substrate without the use of a binder. Silver components in dry form made into a suspension with a binder and applied to a substrate do not provide the same effect because the surfaces of the silver components can be shielded by the binder. In the present application, the combination of the binder-less application of the SILVAGARD silver nanoparticles along with non-agglomerative nature of the SILVAGARD silver nanoparticles allows for the maximum surface area available to interact with odor-causing agents. While the specific mechanisms of this interaction can be multiple and complex, it is thought that the odor-eliminating effectiveness of the SILVAGARD silver nanoparticles is due in large part to the adsorption of odor-causing agents.

The vast number of SILVAGARD silver nanoparticles on the surface of the substrate provides a very large reservoir and surface area of silver for continuous protection. It is this very large surface area of silver that gives SILVAGARD silver nanoparticles effectiveness at very low concentrations, very low cytotoxicity, and long lasting, sustained release.

The composition may contain about 0.5% to about 3%, or about 0.5% to about 1.1%, or 1.1% silver nanoparticles.

Application of Composition

Figure 5:
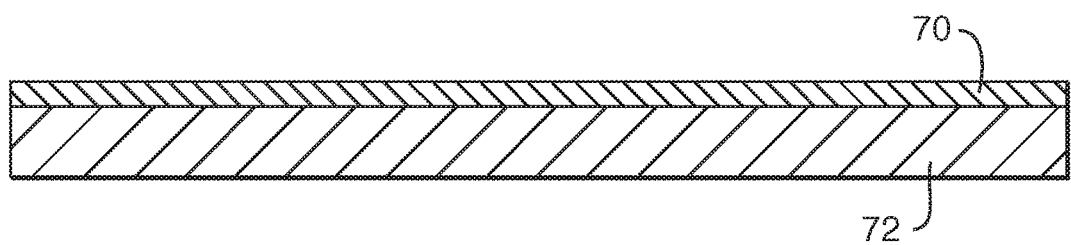
FIG. 5 is a schematic representation of an example of a substrate including the odor elimination feature described herein.

Referring now it FIG. 5, a composition 72 (either the PEG composition, the activated carbon composition, or the silver nanoparticle composition is applied to a suitable substrate, such as a nonwoven substrate 70. Other suitable substrates include spunbond, meltblown, coform, cellulose fluff, cellulose tissue, or polyethylene film.

The nonwoven substrate 70 may be a bonded carded web (BCW), or any other suitable nonwoven or other substrate described herein. In a particular aspect, the BCW is made with two types of fibers; a 3 denier bicomponent fiber with a polyethylene sheath and a polypropylene core and a 6 denier polyester fiber, with a ratio of bicomponent fibers to polyester fibers of 3 to 1.

The composition 72 (either the PEG composition or the activated carbon composition) can be applied to the nonwoven substrate 70 using kiss-roll coating or other printing techniques, spraying, or the like, followed by drying. The dried nonwoven substrate 70 then includes composition 72 attached to the nonwoven substrate fibers. Desirably, for each substrate, and the PEG component is applied at an add-on level of 0.5 to 50%, or more desirably, 1% to 40%; the activated carbon component is added at an add-on level of 2.5% wt/wt. Application may be continuous covering the entire surface of the substrate 70, or may partially cover substrate 70, possibly forming a pattern. The silver nanoparticle component is added at an add-on level of 1.1% wt/wt. Of course, it covers the entire composite due to application by dipping or spraying.

Personal Care Products

Personal care products having an odor control layer of nonwoven substrate 70 may be in the form of diapers, training pants, absorbent underpants, adult incontinence products, and feminine hygiene products. The personal care products may have a bodyside liner, outer cover and/or an absorbent core that includes an odor control layer. Various personal care products are described below.

Feminine Products

A nonwoven substrate 70 including the odor control feature described herein can be included in feminine hygiene products as mentioned above. These include, for example, the pad shown partially cut away in FIG. 1. This pad 10 has a liquid impermeable baffle or outer cover 12 on the side away from the wearer. The baffle 12 is often made from a film like a polyethylene or polypropylene film. The layer closest to the wearer is the liner 14 and is a liquid permeable layer that is preferably soft. Between the baffle 12 and liner 14 there can be a number of layers for different purposes, such as an absorbent core 16 designed to hold the majority of any liquid discharge. Other optional layers include a transfer delay layer or surge layer 17, and tissue or nonwoven wrap sheets (not shown).

Incontinence Products

Disposable absorbent incontinence products are designed to be removed and discarded after a single use. By single use it is meant that the disposable absorbent incontinence product will be disposed of after being used once instead of being laundered or cleaned for reuse, as is typical of regular cloth underwear. Examples of some commercially available disposable absorbent incontinence products include diapers, training pants, pads, pantiliners, fitted briefs, belted shields, guards for men, protective underwear, and adjustable underwear.

Many of the disposable absorbent incontinence underwear are similar in appearance, size, and shape to regular cloth underwear except that they are formed from a variety of different materials including absorbent and elastic materials. The absorbent materials allow the disposable absorbent incontinence underwear to absorb and retain body waste while the elastic material permits the disposable absorbent incontinence underwear to snugly conform to the anatomy of the wearer's torso.

Much of the disposable absorbent incontinence underwear sold today has a unitary configuration that is similar to regular cloth underwear in that the disposable absorbent incontinence underwear is constructed with a waist opening and a pair of leg openings and needs to be pulled onto the body like normal underwear. Another aspect of unitary disposable absorbent underwear is disclosed in U.S. Patent Publication No. 2004/0210205 A1 to Van Gompel et al., which is incorporated herein in its entirety by reference thereto to the extent it does not conflict herewith.

Other disposable absorbent incontinence underwear has an open configuration. By an open configuration it is meant that the disposable absorbent incontinence underwear does not have a waist opening and a pair of leg openings before it is positioned about the wearer's torso. Typically, disposable absorbent incontinence underwear having an open configuration has a relatively flat or convex shape before it is secured around the torso of the wearer. Commonly, disposable absorbent incontinence underwear having an open configuration has an approximately rectangular or hourglass shape. Such products are described in U.S. Pat. No. 4,500,316 to Damico, which is incorporated herein in its entirety by reference thereto to the extent it does not conflict herewith.

An adjustable undergarment, also sometimes referred to as refastenable underwear, has a unitary configuration and can be positioned onto the wearer's body similar to regular cloth underwear. However, the adjustable undergarment has the ability to be opened and then refastened into a closed position during use.

As stated above, disposable absorbent incontinence products are manufactured in a variety of shapes and configurations. Another type of incontinence product is a guard for men, which resembles an absorbent pad that can conform to the male genitalia, as described in U.S. Pat. No. 5,558,659 to Sherrod et al., which is incorporated herein in its entirety by reference thereto to the extent it does not conflict herewith. A belted shield is still another type of a disposable absorbent incontinence product that has an open configuration and is held about the wearer's torso by a belt or a pair of straps, as described in U.S. Pat. No. 5,386,595 to Kuen et al. and U.S. Pat. No. 4,886,512 to Damico et al., which are incorporated herein in their entirety by reference thereto to the extent they do not conflict herewith.

Female incontinence consumers can use various incontinence products similar to or as a variation of those described above, including pads, pantiliners, fitted briefs, belted shields, protective underwear and adjustable underwear.

Figure 2:
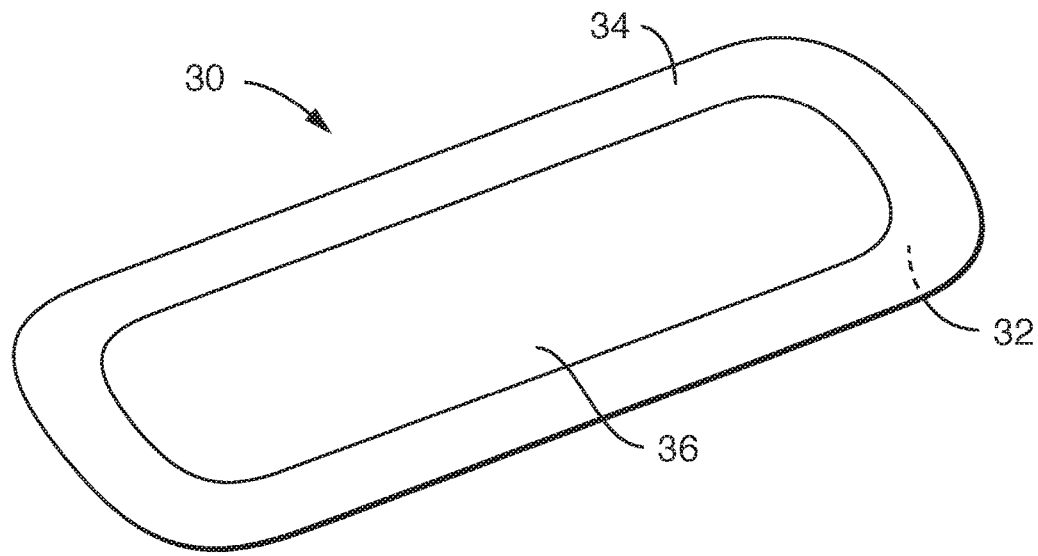
FIG. 2 is a drawing of an adult incontinence product.
Figure 3:
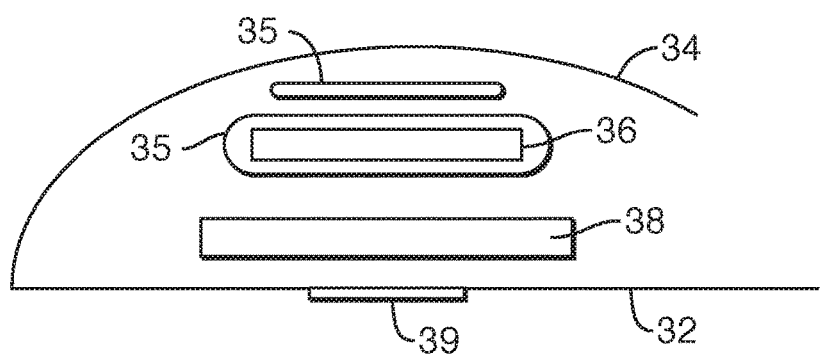
FIG. 3 is a drawing of a cross-section of an adult incontinence product.

Incontinence pads 30 as shown in FIG. 2 likewise have a baffle or outer cover 32, an innermost liner 34, and various layers in between, including the absorbent core 36. FIG. 3 illustrates an incontinence product in cross-section where the section is taken across the narrow part of the product. The liner 34 is at the top, and a surge layer 35 is positioned below the liner 34. The surge layer 35 acts as a reservoir to accept large surges of liquid and slowly release them to the subsequent layers. Below the surge layer 35 is an absorbent core or pledget 36 surrounded by tissue wrap 37. The absorbent core 36 can include superabsorbent particles that are loose and very small and that can escape onto the body or clothing unless contained. The tissue wrap 37 surrounds the absorbent core 36 and keeps the superabsorbent particles from leaving the absorbent core 36. Under the tissue wrapped absorbent core 36 is a fluff layer 38 and then the baffle 32. Many products also have an adhesive strip 39 to help hold the product in place during use by adhering it to the user's underclothes. More information concerning incontinence products can be found, for example, in U.S. Pat. No. 6,921,393 to Tears et al., which is incorporated herein in its entirety by reference thereto to the extent it does not conflict herewith.

The liquid permeable liner 34 is designed to allow body fluid, particularly urine, to quickly pass therethrough and be received by the absorbent core 36. The bodyside liner 34 is placed in contact with the genital area of a human body. The bodyside liner 34 is capable of passing body fluid, voluntarily or involuntarily expelled from the urethra, downward into the absorbent core 36.

Pads typically have an approximately rectangular, hourglass, or asymmetrical configuration having a thickness of about 2.5 centimeters (cm) or less. Desirably, the thickness of a pad is less than about 1 cm. More desirably, the thickness of a pad is less than about 0.7 cm. A pad can have a length of from between about 15 cm to about 50 cm and a width of from between about 2 cm to about 15 cm.

A pantiliner is another female incontinence product. By pantiliner it is meant a thin absorbent product having an approximately rectangular, hourglass or asymmetrical configuration having a thickness of about 1 cm or less. Desirably, the thickness of a pantiliner is less than about 0.9 cm. More desirably, the thickness of a pantiliner is less than about 0.5 cm. A pantiliner can have a length of from between about 15 cm to about 50 cm and a width of from between about 2 cm to about 15 cm.

Absorbent Underpants

Figure 4:
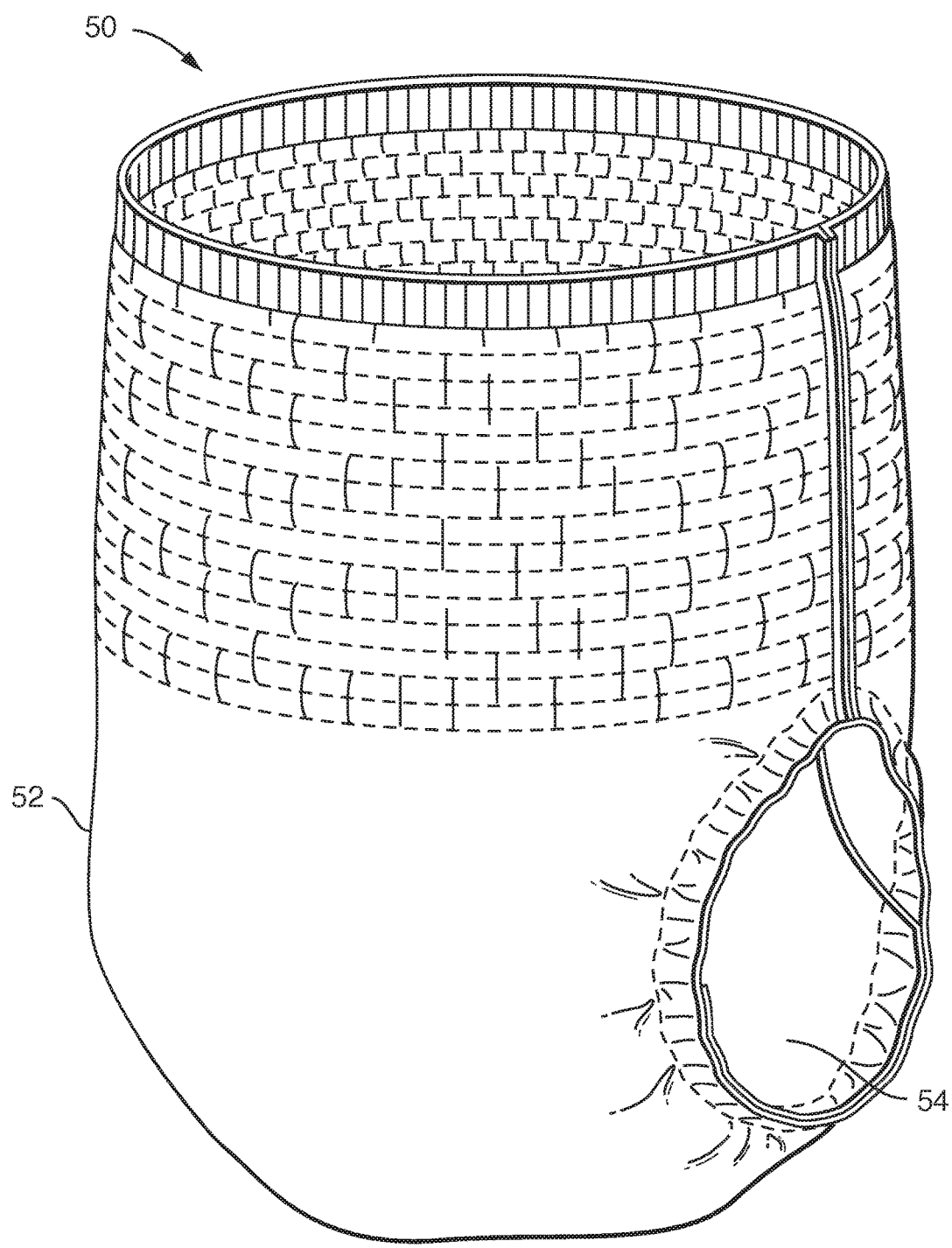
FIG. 4 is a drawing of an absorbent underpant.

Absorbent underpants 50 as shown in FIG. 4 have a baffle 52, a liner 54, and an absorbent core (not shown). Further discussion regarding absorbent underpants can be found, for example, in U.S. Pat. No. 6,240,569 to Van Gompel and in U.S. Pat. No. 6,367,089 to Van Gompel, which are incorporated herein in their entirety by reference thereto to the extent they do not conflict herewith.

The substrate including the odor elimination feature of the present disclosure can be included in any of the personal care products described above as an additional layer to those described, or in the place of a layer described herein.

Application of Treated Substrates to Personal Care Articles

Figure 9:
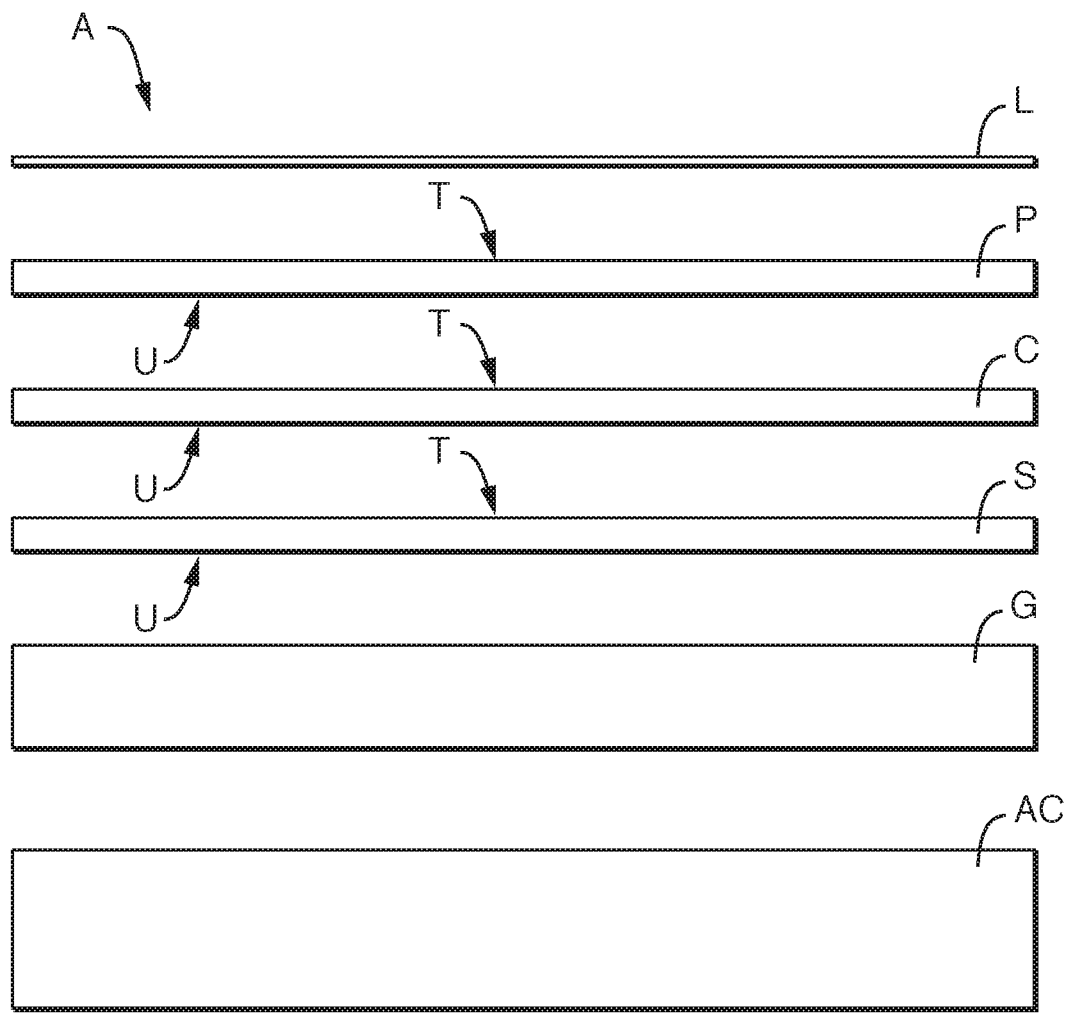
FIG. 9 is a schematic drawing of a layered structure having separate odor eliminating compositions disposed on each layer.

Regardless of the particular form of personal care article, in one aspect the treated substrates are incorporated into a personal care article in layers as seen in FIG. 9. Generally, the layer(s) of treated substrates are located underneath the liner L of the article A in a stacked configuration (if one layer, it is treated with PEG; if two layers, they are treated separately with PEG or (activated carbon or silver nanoparticles); if three layers, they are treated separately with PEG, activated carbon or silver nanoparticles).

Desirably, when three separate treatments are used, each substrate is stacked in the following order, starting with the liner: Liner L, PEG and/or PEG copolymer substrate P, activated carbon substrate C, and silver nanoparticle substrate S. However, any substrate order is acceptable. In addition, there may be more than one layer of the same treatment. Desirably, the treated substrate surfaces T only make contact with untreated substrate surfaces U.

Desirably, the layer(s) of treated substrate are located directly under the liner L, on top of an optional surge layer G. In another aspect (not shown) the layer(s) of treated substrate are located between the surge layer G and the absorbent core A. If desired, surge material could be placed between the PEG and/or PEG copolymer layer P and the activated carbon layer C, or between the activated carbon layer C and the silver nanoparticle layer S.

Figure 10:
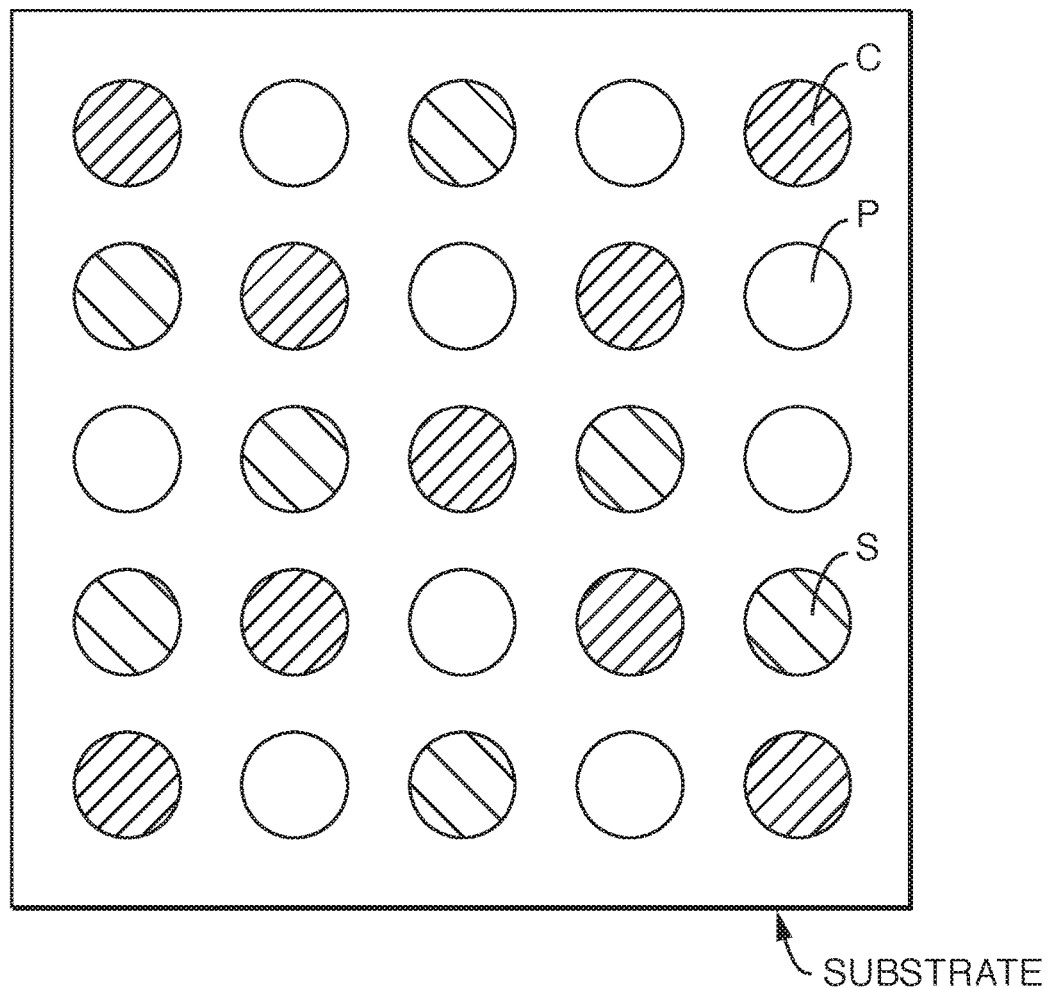
FIG. 10 is an embodiment of a substrate having different odor eliminating compositions applied thereto in an exemplary pattern.

In another aspect of the disclosure, a substrate is treated with both PEG and activated carbon. Desirably, each chemistry is printed or sprayed onto a substrate surface in a spaced apart manner so that they do not blend prior to drying. Referring to FIG. 10, the PEG and/or PEG copolymer and activated carbon compositions may be applied to the same side of the substrate in a pattern, or opposite sides of the substrate (not shown), either in a pattern or with continuous coverage. For example, separate formulations of PEG and/or PEG copolymer, activated carbon and silver nanoparticles may be applied to a nonwoven substrate 70. The PEG and/or PEG copolymer component 73 may be applied to the nonwoven substrate 70 by contacting the nonwoven substrate 70 with an aqueous liquid formulation containing PEG and/or PEG copolymer followed by air drying. The silver nanoparticle component 72 may be applied to the nonwoven substrate 70 by contacting the nonwoven substrate 70 with a non-aqueous liquid formulation containing silver nanoparticles and heptane, or with an aqueous silver nanoparticle solution, followed by air drying.

The dried nonwoven substrate 70 then includes silver nanoparticles attached to the nonwoven substrate fibers. This silver treatment is the SILVAGARD silver nanoparticle process described above. The activated carbon component 74 can be applied to the nonwoven substrate 70 by printing or spraying an activated carbon ink composition to zones of the nonwoven substrate 70. The nonwoven substrate 70 is then air dried. In one aspect, a template or mask can be placed over the nonwoven substrate 70 prior to spraying to allow the spray to produce the zones of a desired chemistry.

The PEG component 73, activated carbon component 74 and the silver component 72 can be applied to the same side of the nonwoven substrate 70; or, the PEG component 73 and activated carbon component 74 can be applied to one side of the nonwoven substrate 70, with the silver component 72 applied to the other side of the nonwoven substrate 70; or, the activated carbon component 74 can be applied to one side of the nonwoven substrate 70, with the silver component 72 and the PEG component 73 and applied to the other side of the nonwoven substrate 70. Each PEG component 73 and activated carbon component 74 of the nonwoven substrate 70 can be separate from each silver component 72 of the nonwoven substrate 70; or the PEG component 73 and activated carbon component 74 can overlap the silver component 72. Other configurations are possible. The PEG component 73, the activated carbon component 74 and the silver component 72 can form alternating stripes (see FIG. 10) or any other shapes or patterns.

Urine Odor Reduction Kit

Human odor can be attributed to skin oils, sweat and volatile compounds emanating from the skin surface. In turn, some of these natural body processes can be affected by heredity, environment, and daily lifestyle activities which allow an individual to produce a characteristic odor. The biological function of body odor production relies on the three types of secretory glands in the human skin. Two of these are normally called the "sweat glands" which are the eccrine and apocrine glands, with the third being the sebaceous glands. The aqueous portion of skin secretions originates mostly from the eccrine sweat glands which consist of entirely water along with dilute salts. The sebaceous glands are closely related with hair follicles and continuously secrete oils, or sebum. Sebaceous glands are found throughout the body, but have a higher concentration in the face and scalp. The apocrine gland is located primarily in the axillary and genital regions.

Characteristic human axillary odors consist of aldehydes (e.g. decanal, nonanal and nonenal), C6 to C11 normal, branched and unsaturated aliphatic acids, alcohol, carbonyls and some steroids as major contributors to body odor malodor. A cleaning composition of the present disclosure may be used to eliminate or reduce human axillary odors.

The cleaning composition is made with an aqueous carrier, and a PEG surfactant such as CETIOL HE, a preservative. A suitable fragrance, one that does not react with actives, may be added, such as one disclosed above. A colorant may be added for aesthetic purposes. Odor removal is enhanced with the addition of activated carbon and/or silver nanoparticles, as discussed herein.

Figure 8:
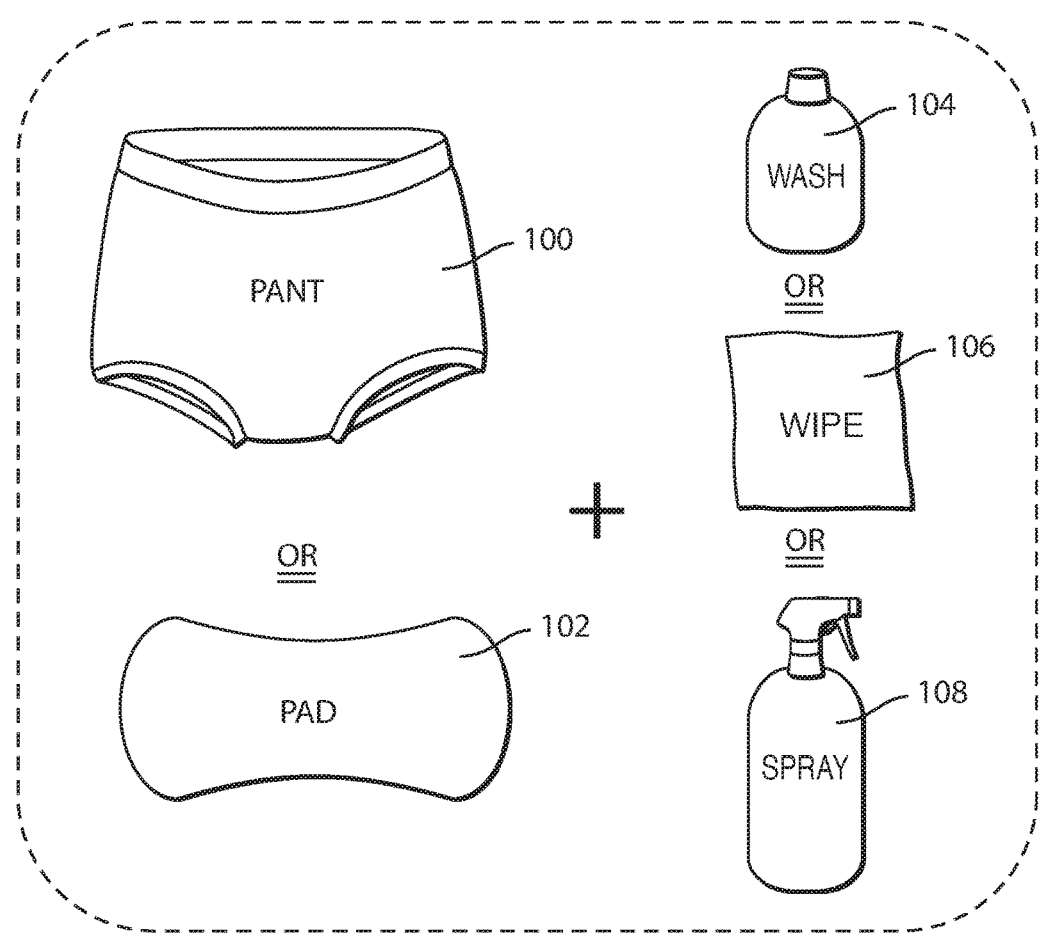
FIG. 8 is one example of a kit according to the present disclosure.

Referring to FIG. 8, in one aspect of the disclosure is a kit that includes a treated personal care product such as the products described above (e.g. pant 100 or pad 102), and a cleaning composition. Desirably, a user will use the cleaning composition to cleanse intimate areas that come into contact with urine prior to donning or applying the personal care product to the body.

The cleaning composition is a combination of PEG and/or PEG copolymers and water. Desirably, it is 12% wt/wt PEG and/or PEG copolymers by weight. It may further include activated carbon and/or silver nanoparticles. The composition is dilute enough to avoid reactions between the non-water components that would prevent of hinder odor reduction.

The cleaning composition may be applied to the body as a wipe 106, a wash 104, or with a spray 108. Thus, the cleaning composition may be included in the kit bottled with spray cap or non-spray cap, or it can be applied to a wipe substrate and packaged in a water-proof material so evaporation cannot readily occur.

Wipe substrates are typically nonwoven materials, such as those used for KLEENEX wipes, manufactured by Kimberly-Clark Corporation, US.

EXAMPLES

The combination of odor-eliminating components described herein has been found to have a synergistic effect in eliminating odors. The combination provides a significantly larger odor reduction that can be achieved by either component alone.

Example Set 1

The procedure for testing the efficacy of PEG derivatives to treat urine odors was as follows:

1. Inject 200 mg of a PEG derivative (liquid or solid phase) into a clean vial (flat bottom headspace crimp top glass vials, 20 ml 25×75 mm, available from Agilent Technologies, Inc., CO, US)

2. If the PEG derivative is in a solid phase, heat vial with the solid PEG derivative to a temperature of 70° C. for 1 hour. This will cause the PEG to transform to a liquid phase. Cool the now liquefied PEG derivative for 3 hours so that it reaches ambient temperature.

3. Cap the vial containing the liquefied PEG derivative.

4. Inject the vial with 1 microliter of isovaleraldehyde using a microsyringe.

5. Incubate the vial at 40° C. for 10 min in an oven (Agilent G1888 Headspace Sampler). Refer to the headspace parameters of TABLE 1, for the oven settings.

6. Remove an aliquot of the headspace (air inside the test tube) and inject it into a gas chromatograph (e.g. Agilent 7890A, available from Agilent Technologies, Inc.). Refer to the gas chromatograph parameters of TABLE 1, for the gas chromatograph settings.

TABLE 1

| Headspace Parameters | | |
|---|---|---|
| Zone temperatures (° C.) | Oven | 40 |
| Event Time (min.) | Gas Chromatograph cycle time | 10.0 |
|  | Equilibration Time | 10.0 |
|  | Inject time | 0.30 |
| GC Paramenters | | |
| Oven | Oven temperature (° C.) | 70 |
|  | Column used | DB-624 |
|  | Run Time (min.) | 10 |
| Detector (FID) | Inlet temp (° C.) | 105 |
|  | Detect temp (° C.) | 250 |

*Column DB-624: 30 m, 0.32 mm Inner Diameter (ID), 1.8μ film. Catalog No. 123-1334, s/n 157858 manufactured by J&W Scientific, Inc. Folsom, CA.

7. An empty standard test tube, the control, is tested to define 0% odor removal.

8. A test tube containing a sample is then tested by removing an aliquot of headspace and injecting it into the gas chromatograph. The peak area for the particular odorous gas obtained from the sample is compared to the peak area from the control. Comparison of the results are presented as "% odor reduction" in TABLE 2.

TABLE 2

| PEG | | | ODOR REDUCTION % | |
|---|---|---|---|---|
| (n) | Code Name | avg | std dev | std. err |
| | Control (Blank) | | | |
| 5 | PEG 200 | 83.8 | 3.5 | 2.0 |
| 7.5 | PEG 300 | 84.6 | 3.3 | 1.9 |
| 10 | PEG 400 | 83.0 | 3.4 | 2.0 |
| 25 | PEG 1000 | 55.1 | 9.5 | 5.5 |
| 40 | PEG 2000 | 14.7 | 17.9 | 10.3 |
| 80 | PEG 4000 | 15.8 | 17.1 | 9.9 |
| 40 | PEG 40 stearate (~PEG 2000) | 42.7 | 11.6 | 6.7 |
| 100 | PEG 100 stearate (~PEG 5000) | 36.0 | 13.4 | 7.7 |
| 4 | BRIJ 30 | 89.3 | 2.2 | 1.3 |
| 7 | CETIOL HE | 86.7 | 2.4 | 1.4 |
| 9.5 | TRITON X-100 | 83.2 | 2.9 | 1.7 |
| 20 | TWEEN 20 | 83.5 | 3.5 | 2.0 |
| 20 | TWEEN 60 | 65.1 | 7.5 | 4.3 |
| 0 | Distilled water | 36.7 | 12.8 | 7.4 |

Figure 6:
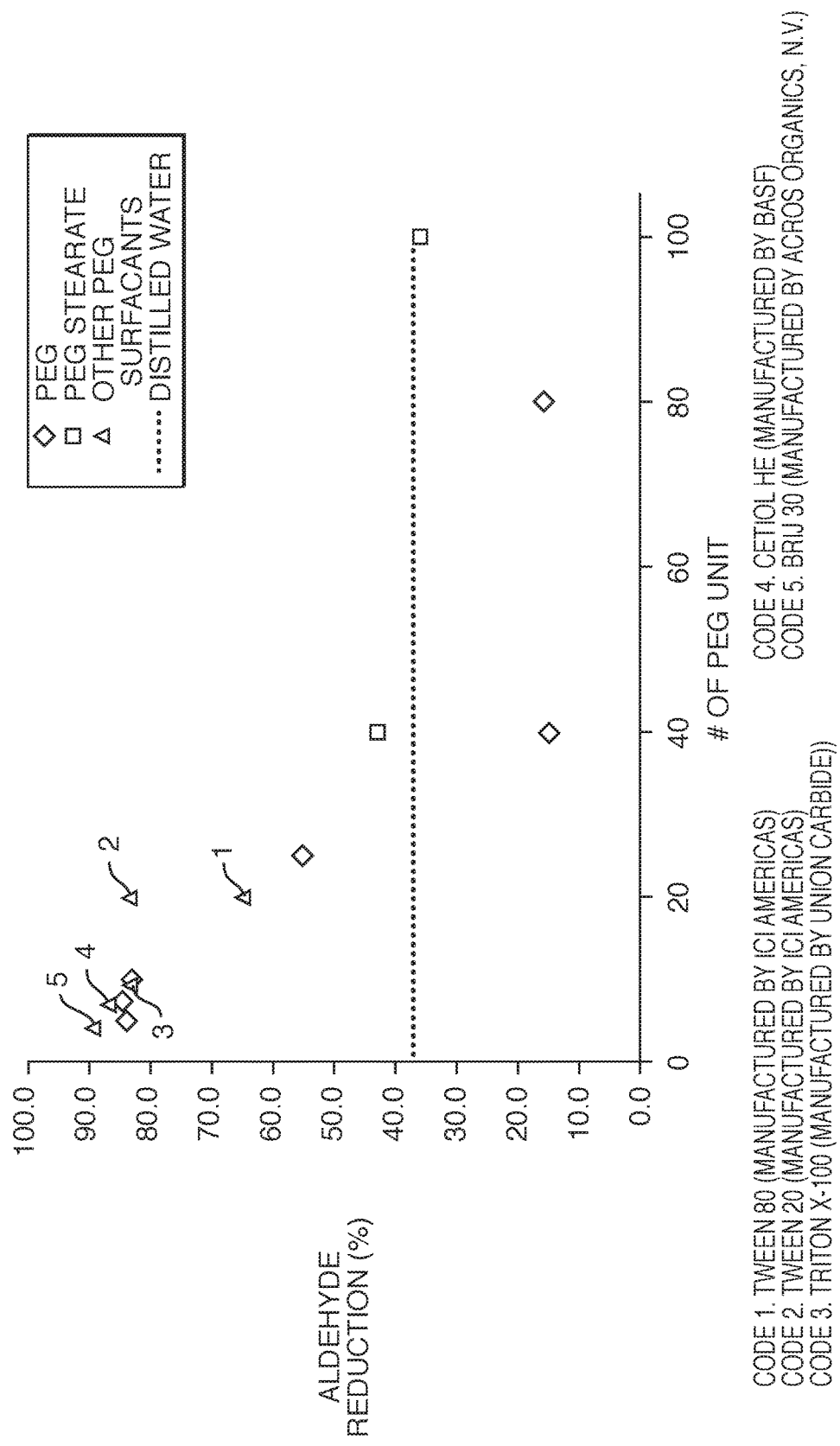
FIG. 6 is a chart illustrating the results of odor testing with different odor eliminating substances.

The results from TABLE 2 are shown in the chart of FIG. 6. The PEG or PEG copolymers having an n<=20 performed best to reduce urine odors.

Example Set 2

POISE incontinence pads available from Kimberly-Clark Corp. of Dallas, Tex. USA with the label "Moderate Absorbency" were purchased from a local store for a urine odor ranking panel (ORP) study. The surge layer (BCW) was removed from each pad to make space to accommodate 0.9 osy BCW fabrics treated with the compositions of the disclosure. Three pieces of BCW were inserted into the pads where the original layer was removed. For the control codes three layers of untreated BCW were placed into the pads. For the treated codes each "treatment" was applied to separate BCW layers and inserted into the pads as described in TABLE 3. For pads with either one or two treatments, untreated BCW layers were also inserted into the pads in order to ensure each pad had three BCW layers. After inserting the BCW layers, the top liner was pulled back into place and one staple was applied at the middle edge of the pad to hold the contents in place.

Human urine was collected, pooled, filter sterilized, and then inoculated with bacteria (*Proteus mirabilis, Klebsiella pnuemonae, E. faecalis*, and *E. coli*). A fixed amount of urine (78 ml) was placed on each pad and the pad was incubated at 37° C. for four hours. Ten panelists were then exposed to each of the seven codes and asked to rank them for overall odor. The urine odor intensity ranking results are shown in TABLE 3, in which the controls were the pad insulted with urine and the pad insulted with water. Codes with rankings above the urine control were judged to produce fewer odors. The CETIOL HE sample ranked first.

TABLE 3

| Sample ID | BCW Add-on level (% wt/wt) | Urine Odor Intensity Ranking |
|---|---|---|
| Control - Urine | na | 2.9 |
| Control - Water | na | 6.2 |
| PEG 300 | 14 | 3.2 |
| Cetiol 1414 | 14 | 2.5 |
| Cetiol HE | 14 | 4.3 |

Figure 7B:
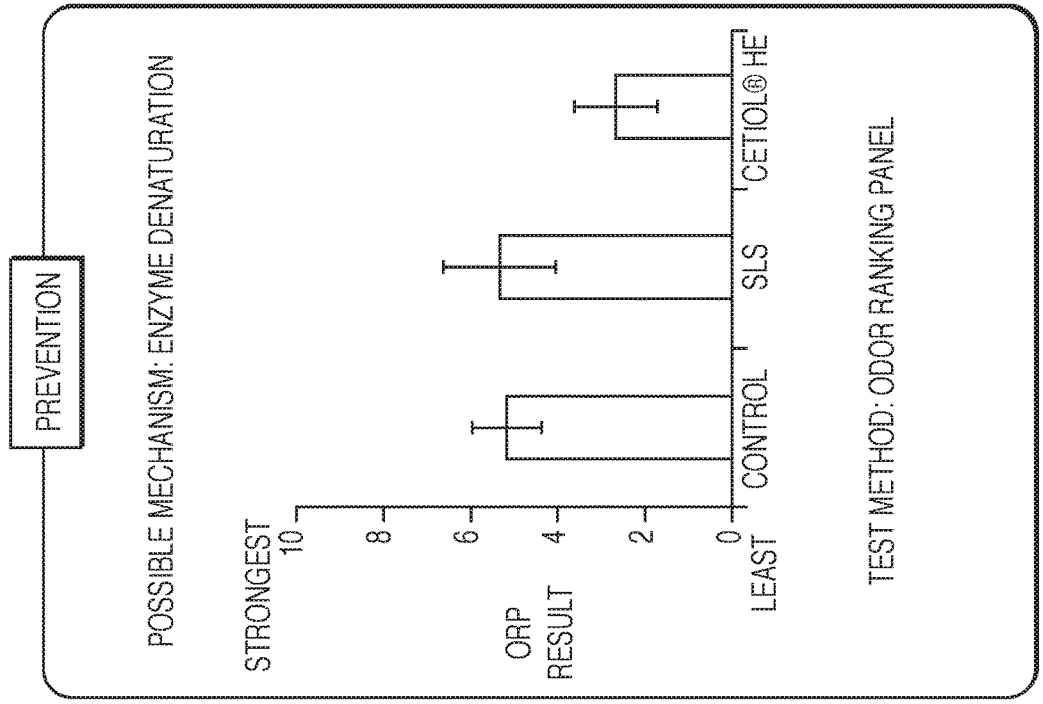
FIG. 7A-C are charts illustrating the results of odor testing with different odor eliminating substances.
Figure 7A:
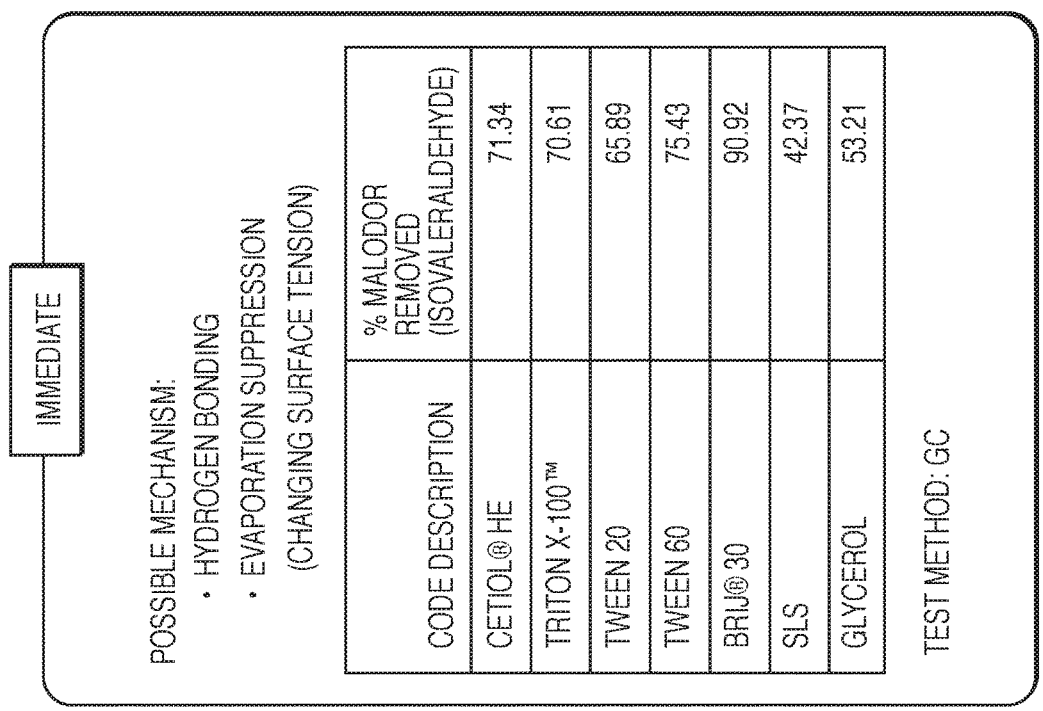

Without being bound by theory, there are three possible mechanisms by which the PEG component of the composition reduce aldehydes. In one theory, it is thought that hydrogen bonding to the aldehyde may be induced by the —OH group of the PEG surfactant. To verify this effect, odor efficacy was evaluated using gas chromatography. The following chemicals were tested: five types of PEG surfactants, (CETIOL HE, TRITON X-100™, TWEEN 20, TWEEN 60 and BRIJ 30 (see Table 2)); 1 ionic surfactant (Sodium laureth sulfate, SLS); and Glycerol. (Glycerol is not used as a surfactant, but was tested because it can induce hydrogen bonding with aldehydes.) To simulate urine odor reduction, ethyl mercaptan and isovaleraldehyde were selected as the representative odor of sulfur compounds and aldehydes. 2 µL of each odorant and 100 µL of each chemical were injected into a 25 mL gas chromatograph test tube and capped for testing. The odor reduction efficacy is listed in FIG. 7A. As expected, the PEG surfactants demonstrated better aldehyde reduction than the ionic surfactant, SLS. It is thought that the difference between the PEG surfactant and SLS may be caused by the hydrogen bonding.

Figure 7C:
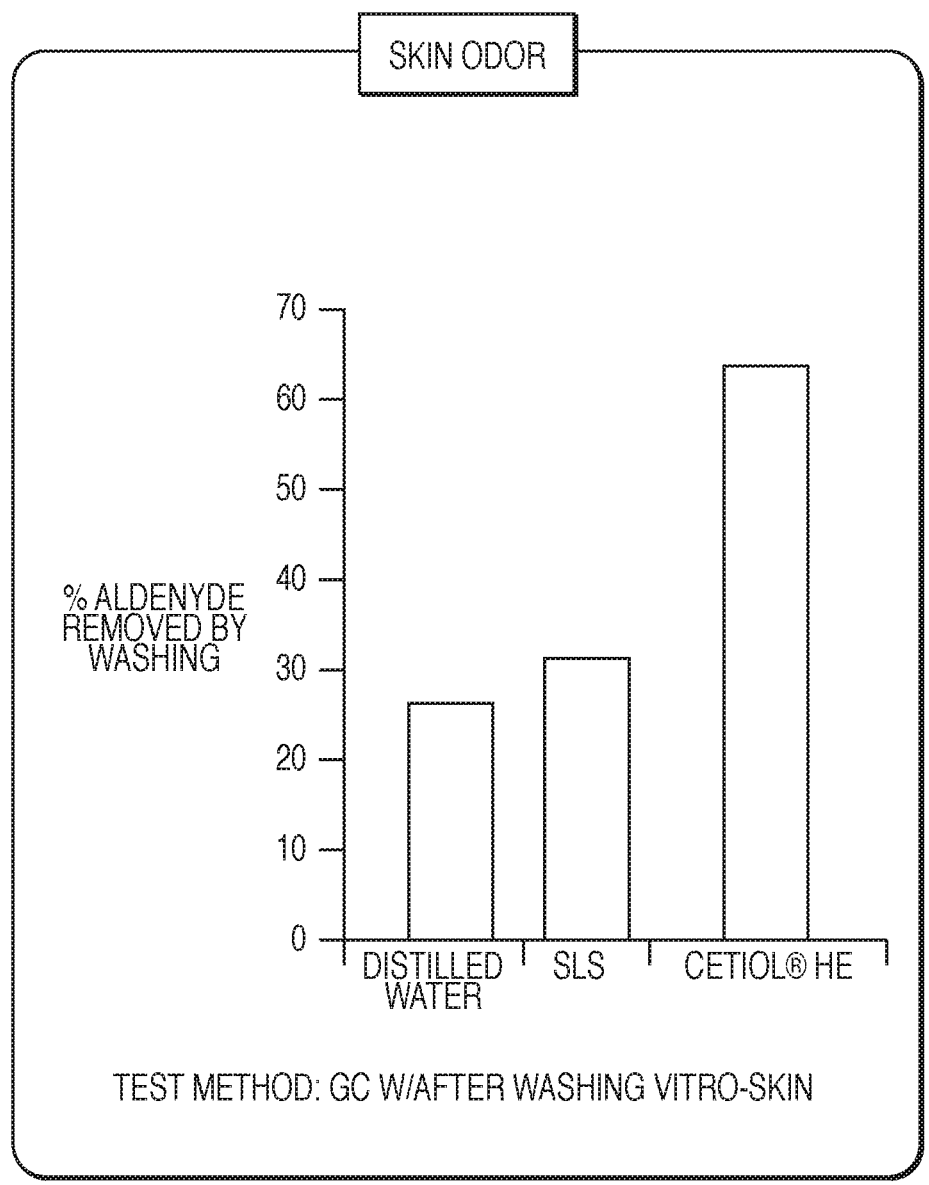

In yet another theory, exploration is based on the fact that surfactants denaturize protein. Treatment with a surfactant can lead to protein denaturation in the form of protein dissociation, precipitation, and fragmentation. This denaturation may influence a broad spectrum of proteins and enzymes. By denaturation of proteins, one can expect a reduction of the odor formation, which is mainly caused by bacteria and enzymes. See FIG. 7B In another theory, the exploration is based on the fact that surfactants modify surface tension and suppress evaporation of water or other volatiles. Referring to FIG. 7C, glycerol demonstrates lower efficacy than PEG surfactants in aldehyde reduction. Considering the fact that glycerol also can interact with aldehyde by hydrogen bonding, the difference between glycerol and PEG surfactants may be due to the surface property that the surfactant changed. In the reduction of ethyl mercaptan, all surfactants including SLS showed better reduction than glycerol, which may be explained as the suppression of evaporation by surfactants.

Experimental Set 3

POISE incontinence pads available from Kimberly-Clark Corp. of Dallas, Tex. USA with the label "Moderate Absorbency" were purchased from a local store for a urine odor ranking panel (ORP) study. The surge layer (BCW) was removed from each pad to make space to accommodate 0.9 osy BCW fabrics treated with the compositions of the disclosure. Three pieces of BCW were inserted into the pads where the original layer was removed; separate BCW layers were inserted into the pads as described in TABLE 4. For Code 1, three layers of urine treated BCW were placed into the pads (see urine description in Experimental Set 2). For Code 2, three layers of untreated BCW were placed into the pads. For Code 3, one layer of CETIOL HE treated BCW was placed over two untreated layers of BCW. For Code 4, one layer of AC ink treated BCW was placed over a SILVAGARD treated layer and an untreated layer of BCW. For Code 5, one layer of AC ink treated BCW was placed over a SILVAGARD treated layer and a CETIOL HE layer of BCW. For Code 6, one layer of AC ink treated BCW was placed over a CETIOL HE layer and an untreated layer of BCW. After inserting the BCW layers into the pad, the top liner was pulled back into place and one staple was applied at the middle edge of the pad to hold the contents in place.

In the PEG treated layer, CETIOL HE was diluted with distilled water to make a 25% solution and applied to the BCW at an add-on rate of 14% wt/wt (after air-drying) using a PREVAL Spray gun (Coal City, Ill.) and air dried.

In the silver treated layer, silver was applied to the BCW by soaking it in a liquid formulation containing SILVA-GARD silver nanoparticles and heptane, followed by air drying. The dried BCW contained silver nanoparticles attached to the BCW fibers.

In the activated carbon treated layer, activated carbon was applied to the BCW by spraying it with an activated carbon ink. The ink is applied using a grill grate as a mask to form stripes on the BCW. The zone-sprayed BCW was then air dried.

TABLE 4 shows the addition of CETIOL HE to other malodor reducing technologies, such as activated carbon ink by itself or activated carbon ink with SILVAGARD, results in boosting the urine odor intensity reduction as scored by the panelists. The code with active carbon, silver nanoparticles and CETIOL HE performed best.

TABLE 4

| Code | Sample Layers (Listed top (body-facing) to bottom (garment-facing)) | Active BCW add-on % wt/wt | Urine odor intensity ranking |
|---|---|---|---|
| 1 | Control - Three urine-treated | Na | 2.2 |
| 2 | Control - Three water-treated | Na | 7.0 |
| 3 | CETIOL HE + two untreated | +14 | 3.2 |
| 4 | AC ink + SILVAGARD + one untreated | 8.3 solids (=2.4 carbon) 1.1 silver | 4.1 |
| 5 | AC Ink + SILVAGARD + CETIOL HE | 8.3 solids (=2.4 carbon) 1.1 silver + 14 | 4.7 |
| 6 | AC ink + CETIOL HE + one untreated | 8.3 solids (=2.4 carbon) + 14 | 3.0 |

The combination of odor-eliminating components has been found to have a synergistic effect in eliminating odors. The combination provides a significantly larger odor reduction that can be achieved by either component alone, even at higher concentrations. If other forms of silver (e.g., silver/zeolite) or even other forms of silver nanoparticles (e.g., silver nanoparticle dispersion stabilized by a binder) are used, the synergistic effect is largely absent.

Experimental Set 4

Described is a semi-quantitative analytical method for the determination of the headspace concentration of gases in closed containers using a DRÄGER tube (Dräger Safety Inc., Pittsburgh, Pa.).

This method is an in vitro method effective for screening and evaluating full products, usually prior to confirmation with the other quantitative analytical methods or odor ranking panel human perception studies. Though the gas chromatograph headspace method, described herein, gives quantitative results, it cannot be used to test full products because it has a limited sample holder capacity of only 20 cc, not enough for a full product.

DRÄGER tubes are glass vials filled with a chemical reagent that reacts via a color change (e.g. to blue) with a specific chemical or family of chemicals. DRÄGER tube detection-limits are typically above the human threshold, and tube types, i.e. the number of chemicals that can be detected are limited. Detection and accuracy is dependent on the chemical type. A known volume of gaseous sample (1000 cc headspace air per stroke) is drawn through the tube using the DRÄGER ACCURO bellows pump. If the targeted chemical(s) is present in the tested environment the tube changes color. The extent of the color change indicates the measured concentration in the headspace, typically in parts per million (ppm).

In this test, 1 inch by 7 inch (1"×7") strips of BCW were spray coated (PREVAL spray gun) with undiluted CETIOL HE. The strips were placed in the jars, as described above. The control jars either had no sample in them or 1"×7" strips of untreated BCW. 40 µl of acetaldehyde (Sigma-Aldrich Chemical Co., Milwaukee Wis.) was injected into the jar via a septum in the lid of the jar. The jars were allowed to stand for 40 minutes, at ambient temperature, before measurement of the headspace concentration using acetaldehyde DRÄGER tubes. These tests were conducted in duplicate.

The results of the DRÄGER tube tests are shown in TABLE 5. The treated BCW demonstrates a 50% reduction of acetaldehyde versus the control. This shows that the CETIOL HE urine odor reduction technology reduces the urine malodor by removing the aldehydes.

TABLE 5

| Sample | Acetaldehyde (40 µL) (Ppm) |
|---|---|
| Control Empty jar | 100 |
| Control - BCW untreated | 100 |
| CETIOL HE treated BCW (14% wt/wt) | 50 |

It should be understood, of course, that the foregoing relates only to certain disclosed embodiments of the present disclosure and that numerous modifications or alterations may be made therein without departing from the spirit and scope of the disclosure as set forth in the appended claims.

What is claimed:

1. A personal care product comprising a first aldehyde odor control layer that comprises an odor control composition comprising a polyethylene glycol surfactant selected from the group consisting of laureth-4, polysorbate 20, myreth-3 myristate, octoxynol-9, polyethylene glycol-7 glyceryl cocoate, and any combination thereof; wherein the personal care product includes a liner and an absorbent core; wherein the first aldehyde odor control layer is located between the liner and the absorbent core; and wherein the polyethylene glycol surfactant comprises 25% to 40% of the odor control composition.

2. The personal care product of claim 1 wherein the polyethylene glycol surfactant has a number of polymer units less than or equal to 20.

3. The composition of claim 1 wherein the polyethylene glycol surfactant has a number of polymer units less than or equal to 10.

4. The personal care product of claim 1 wherein the polyethylene glycol surfactant has a number of polymer units less than or equal to 5.

5. The personal care product of claim 1 wherein the odor control composition comprises 60% to 90% water.

6. The personal care product of claim 1 wherein the odor control composition further comprises at least one of a thickener, a preservative, and a fragrance.

7. The personal care product of claim 1 wherein the odor control composition is applied to the first aldehyde odor control layer at an add-on level of 0.5% to 50%.

8. The personal care product of claim 1 wherein the odor control composition is applied to the first aldehyde odor control layer at an add-on level of 1.0% to 40%.

9. The personal care product of claim 1 wherein the odor control composition is applied to a surface of a substrate, and the odor control composition continuously covers the surface of the substrate.

10. The personal care product of claim 1 wherein the personal care product is in a form selected from the group consisting of diapers, training pants, absorbent underpants, adult incontinence products, and feminine hygiene products.

11. A personal care product comprising a first aldehyde odor control layer that comprises an odor control composition comprising a polyethylene glycol surfactant selected from the group consisting of laureth-4, polysorbate 20, myreth-3 myristate, octoxynol-9, polyethylene glycol-7 glyceryl cocoate, and any combination thereof; wherein the personal care product includes a liner and an absorbent core; wherein the first aldehyde odor control layer is located between the liner and the absorbent core; and wherein the odor control composition is applied to a surface of a substrate, and the odor control composition continuously covers the surface of the substrate.

12. The personal care product of claim 11 wherein the polyethylene glycol surfactant has a number of polymer units less than or equal to 20.

13. The composition of claim 11 wherein the polyethylene glycol surfactant has a number of polymer units less than or equal to 10.

14. The personal care product of claim 11 wherein the polyethylene glycol surfactant has a number of polymer units less than or equal to 5.

15. The personal care product of claim 11 wherein the odor control composition comprises 60% to 90% water.

16. The personal care product of claim 11 wherein the odor control composition further comprises at least one of a thickener, a preservative, and a fragrance.

17. The personal care product of claim 11 wherein the odor control composition is applied to the first aldehyde odor control layer at an add-on level of 0.5% to 50%.

18. The personal care product of claim 11 wherein the odor control composition is applied to the first aldehyde odor control layer at an add-on level of 1.0% to 40%.

19. The personal care product of claim 11 wherein the wherein the polyethylene glycol surfactant comprises 25% to 40% of the odor control composition.

20. The personal care product of claim 11 wherein the personal care product is in a form selected from the group consisting of diapers, training pants, absorbent underpants, adult incontinence products, and feminine hygiene products.

* * * * *